United States Patent
Koeda

(10) Patent No.: US 9,157,055 B2
(45) Date of Patent: Oct. 13, 2015

(54) BIOCHIP, SAMPLE REACTION APPARATUS, AND SAMPLE REACTION METHOD

(75) Inventor: Hiroshi Koeda, Suwa (JP)

(73) Assignee: Seiko Epson Corporation (JP)

( * ) Notice: Subject to any disclaimer, the term of this patent is extended or adjusted under 35 U.S.C. 154(b) by 1257 days.

(21) Appl. No.: 13/014,056

(22) Filed: Jan. 26, 2011

(65) Prior Publication Data

US 2011/0189660 A1　Aug. 4, 2011

(30) Foreign Application Priority Data

Feb. 2, 2010　(JP) ................ 2010-020953

(51) Int. Cl.
*G01N 21/75* (2006.01)
*C12M 1/34* (2006.01)
*C12Q 1/68* (2006.01)

(52) U.S. Cl.
CPC ... *C12M 1/34* (2013.01); *C12Q 1/68* (2013.01)

(58) Field of Classification Search
None
See application file for complete search history.

(56) References Cited

U.S. PATENT DOCUMENTS

| 6,063,589 A * | 5/2000 | Kellogg et al. ................. 435/24 |
| 6,527,432 B2 * | 3/2003 | Kellogg et al. ............ 366/182.1 |
| 7,998,433 B2 * | 8/2011 | Park et al. ..................... 422/500 |
| 8,696,992 B2 * | 4/2014 | Tajima ....................... 422/82.05 |
| 2003/0138353 A1 * | 7/2003 | Bargoot et al. ................. 422/58 |
| 2010/0243078 A1 | 9/2010 | Yoo |

FOREIGN PATENT DOCUMENTS

| JP | 10-174600 A | 6/1998 |
| JP | 2009-136250 | 6/2009 |
| WO | WO-2009-066897 A2 | 5/2009 |

* cited by examiner

*Primary Examiner* — Ann Lam

(74) *Attorney, Agent, or Firm* — Harness, Dickey & Pierce, P.L.C.

(57) ABSTRACT

A biochip includes: a first chamber; a second chamber filled with a wax, a melting point of the wax being 25° C. or more and 63° C. or less; an injection path between the first chamber and the second chamber; and a sub-chamber that includes a wall at least partially made of the wax, the sub-chamber is formed inside the second chamber and communicates with the first chamber via the injection path.

6 Claims, 5 Drawing Sheets

BIOCHIP, SAMPLE REACTION APPARATUS, AND SAMPLE REACTION METHOD

CROSS-REFERENCE

This application claims priority to Japanese Patent Application No. 2010-020953, filed Feb. 2, 2010, the entirety of which is hereby incorporated by reference.

BACKGROUND

1. Technical Field

The present invention relates to a biochip, a sample reaction apparatus, and a sample reaction method.

2. Related Art

In recent years, the existence of genes associated with various diseases has been revealed, and attention has been focused on the medical care utilizing genes, including genetic diagnosis, gene therapy, etc. Also in the fields of agriculture and stock raising, a number of approaches utilizing genes have been developed for breed distinction and selective breeding. Gene application techniques are thus expanding. For utilizing genes, nucleic acid amplification techniques have widely spread. As an example of such a technique, PCR (Polymerase Chain Reaction) is generally known. PCR is now an indispensable technique for elucidating the information of biological substances.

In PCR testing, a container for sample reactions, which is called a tube or a chip (biochip), is commonly used to perform the reaction. However, such an approach has problems in that a large amount of reagent or the like is required, the apparatus is complicated in order to achieve the required thermal cycle, and the reaction takes a long period of time. Therefore, there has been a demand for a biochip and a reaction apparatus for performing PCR accurately within a short period of time using very small amounts of reagent and sample.

In order to solve such a problem, JP-A-2009-136250 discloses an apparatus where a reaction liquid in the form of droplets is moved back and forth in a tube filled with a liquid (mineral oil, etc.) that is immiscible with the reaction liquid and has a lower specific gravity than the reaction liquid, thereby applying a thermal cycle to the reaction liquid to perform a reaction.

However, in the biochip described in JP-A-2009-136250, a very small amount of liquid sample has to be accurately dispensed into a plurality of chambers, so operation with skill and accuracy is required. Further, because the biochip is filled with mineral oil, some ingenuity is necessary to prevent the liquid from leaking or evaporating during storage or handling, such as the provision of a valve, a seal, etc.

SUMMARY

An advantage of some aspects of the invention is to provide a biochip that allows a liquid sample to be accurately dispensed in a simple manner and suppresses liquid leakage or evaporation during storage or handling, a sample reaction apparatus, and a sample reaction method.

(1) A biochip according to an aspect of the invention includes a first chamber, a second chamber filled with a wax, a melting point of the wax being 25° C. or more and 63° C. or less, an injection path between the first chamber and the second chamber, and a sub-chamber that includes a wall at least partially made of the wax, the sub-chamber is formed inside the second chamber and communicates with the first chamber via the injection path.

According to this aspect of the invention, the second chamber is filled with the wax that is solid at room temperature (25° C.) or less. Therefore, liquid leakage or evaporation is suppressed, and this facilitates the handling and storage of the biochip. Further, the wax is liquid (oil) at a temperature range where PCR is performed. Therefore, the reaction can be performed easily without the need for a special treatment.

According to this aspect of the invention, the sub-chamber that includes a wall at least partially made of the wax is formed inside the second chamber, and the sub-chamber communicates with the first chamber via the injection path. As a result, using centrifugal force or the like, a liquid sample supplied to the first chamber is easily dispensed in a precise amount to the sub-chamber via the injection path.

(2) It is preferable that the biochip includes a plurality of sets, each one of the set including the second chamber and the injection path, the injection paths are in one plane and disposed radially from a point in the plane, and the first chamber is closer to the point than the injection paths.

As a result, the biochip enables a liquid sample to be dispensed easily and accurately using centrifugal force or the like even when the biochip includes a plurality of second chambers.

(3) It is preferable that, in the biochip, a primer and/or a fluorescent probe is disposed in the sub-chamber.

As a result, if a liquid sample is dispensed to the sub-chamber, the liquid sample is mixed with the primer and/or a fluorescent probe. This further facilitates the dispensing operation.

(4) It is also preferable that, in the biochip, a primer and/or a fluorescent probe is disposed in the second chamber farthest from the injection path.

As a result, the liquid sample is mixed more easily with the primer and/or the fluorescent probe. Further, the primer and/or the fluorescent probe are less likely to flow out into the first chamber.

(5) A sample reaction apparatus according to another aspect of the invention is a sample reaction apparatus using a biochip. The biochip includes a first chamber, a second chamber filled with a wax, a melting point of the wax being 25° C. or more and 63° C. or less, an injection path between the first chamber and the second chamber, and a sub-chamber that includes a wall at least partially made of the wax, the sub-chamber is formed inside the second chamber and communicates with the first chamber via the injection path. The sample reaction apparatus includes a holder that holds the biochip; a rotor that rotates the biochip in a case the holder holds the biochip to vary the distance between a gravitationally lowest point in the second chamber and the axis of rotation; and a heating unit that heats at least a part of the second chamber in a case the holder holds the to a temperature not less than the melting point of the wax so that the biochip has a symmetrical temperature distribution about the axis of rotation.

According to this aspect of the invention, if the biochip is rotated, the distance between a gravitationally lowest point in the second chamber and the axis of rotation varies. Additionally, the heating unit allows the formation of a symmetrical temperature distribution about the axis of rotation. As a result, a sample reaction apparatus that efficiently performs a sample reaction using a biochip that allows a liquid sample to be accurately dispensed in a simple manner.

(6) A sample reaction method according to a further aspect of the invention is a sample reaction method using a biochip. The biochip includes a first chamber, a second chamber filled with a wax, a melting point of the wax being 25° C. or more and 63° C. or less, an injection path between the first chamber and the second chamber, a sub-chamber that includes a wall at least partially made of the wax, the sub-chamber is formed inside the second chamber and communicates with the first chamber via the injection path and has a wall at least partially made of the wax. The sample reaction method includes supplying a liquid sample to the first chamber; filling the sub-chamber with the liquid sample by rotating the biochip about an axis of rotation to generate centrifugal force from the first chamber to the injection path; and performing a sample reaction by heating at least a part of the second chamber to a temperature not less than the melting point of the wax so that the biochip has a symmetrical temperature distribution about the axis of rotation, and then rotating the biochip to vary the distance between a gravitationally lowest point in the second chamber and the axis of rotation.

According to this aspect of the invention, the biochip, in which the sub-chamber that includes a wall at least partially made of the wax has formed inside the second chamber, is rotated to apply centrifugal force thereto from the first chamber to the injection path, whereby the liquid sample can be dispensed accurately and easily from the first chamber to the sub-chamber.

Further, according to this aspect of the invention, the sample reaction method enables to perform a sample reaction efficiently using a biochip that allows a liquid sample to be accurately dispensed in a simple manner, in which the biochip is rotated to vary the distance between a gravitationally lowest point in the second chamber and the axis of rotation, and also the biochip is heated to form a temperature distribution in the second chamber.

BRIEF DESCRIPTION OF THE DRAWINGS

The invention will be described with reference to the accompanying drawings, wherein like numbers reference like elements.

DESCRIPTION OF EXEMPLARY EMBODIMENTS

Hereinafter, preferred embodiments of the invention will be described in detail with reference to the drawings. The embodiments described below do not limit the subject matter of the invention defined in the claims. Not all the configurations described below are essential constituent features of the invention.

1. Biochip of First Embodiment

Figure 1A:
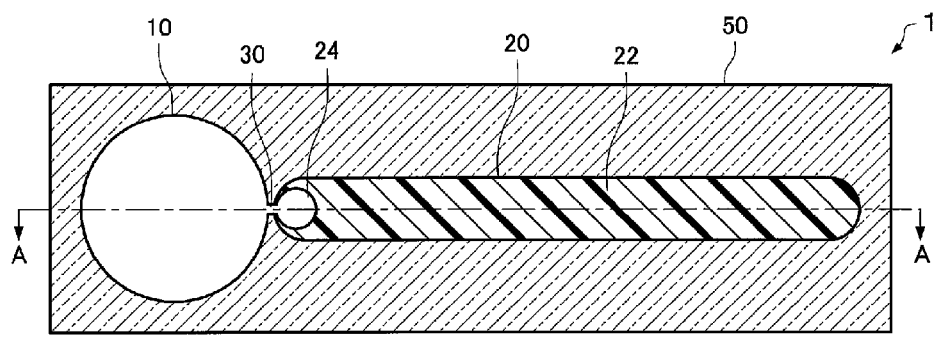
FIG. 1A is a plan view of a biochip according to a first embodiment.
Figure 1B:
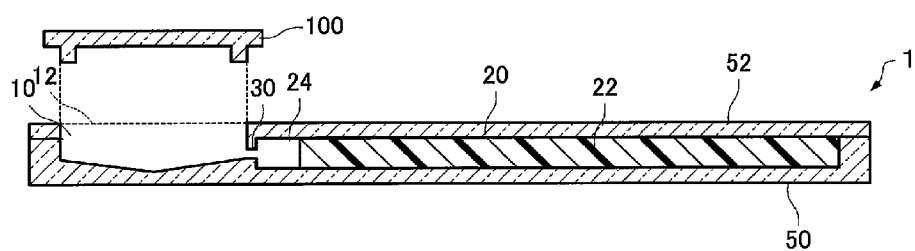
FIG. 1B is a cross-sectional view along line A-A of FIG. 1A.

FIG. 1A is a plan view of a biochip according to the first embodiment, and FIG. 1B is a cross-sectional view along line A-A of FIG. 1A.

The biochip 1 according to the first embodiment includes a first chamber 10, a second chamber 20, and an injection path (orifice) 30. The first chamber 10 and the second chamber 20 communicate with each other via the injection path 30.

The first chamber 10 is formed as a recess in a substrate 50. The first chamber 10 is configured to allow a liquid sample (a liquid that contains a sample) to enter through an inlet 12. The first chamber 10 may be configured to allow the inlet 12 to be closed with a cap 100.

When the biochip 1 is used for PCR, the liquid sample is an analyte-containing liquid that may contain a target nucleic acid. Examples of target nucleic acids include DNA extracted from samples such as blood, urine, saliva, and cerebrospinal fluid and cDNA obtained by reverse transcription of RNA extracted from such samples. The liquid sample may contain a primer for amplifying a target nucleic acid and/or a fluorescent probe for detecting a PCR product.

The second chamber 20 is formed in the substrate 50. In the example shown in FIG. 1A and FIG. 1B, the second chamber 20 is in the form of a tube whose longitudinal direction extends in the direction from the first chamber 10 to the injection path 30. The shape of the second chamber 20 is not limited thereto. For example, the second chamber 20 may be in the form of a tube including a bent portion where the tube is bent at a certain angle. The second chamber 20 may also have a partition portion that partitions a part of the inner region of the second chamber 20, forming a channel that goes around the partition portion.

The second chamber 20 is filled with a wax 22. The second chamber 20 also has formed therein a sub-chamber 24. The sub-chamber 24 communicates with the first chamber 10 via the injection path 30, and the wall of the sub-chamber 24 is at least partially made of the wax 22.

The wax 22 preferably has a melting point within such a temperature range that the wax 22 is solid when the biochip is stored or transported and a liquid sample is dispensed, while it is liquid at the time of a sample reaction. In many cases, the room temperature at which a liquid sample is dispensed is usually set at about 25° C. Therefore, it is preferable that the melting point of the wax 22 is 25° C. or more and 63° C. or less. The body temperature of the operator who dispenses a liquid sample is usually about 37° C. Therefore, it is more preferable that the melting point of the wax 22 is 37° C. or more. In the case where the biochip is handled in a temperature environment of 25° C. until a sample reaction, the melting point of the wax may be less than 25° C.

In the PCR thermal cycle, the annealing temperature is lowest and it is about 63° C. in the high-temperature case, so it is preferable that the melting point of the wax 22 is 63° C. or less. In the PCR thermal cycle, the annealing temperature is about 55° C. in the low-temperature case, so it is more preferable that the melting point of the wax 22 is 55° C. or less.

As a wax having such a melting point, Paraffin Wax 115 manufactured by NIPPON SEIRO is usable, for example. Paraffin Wax 115 has a melting point of 47° C., and has a viscosity of 3 cP and a density of 0.768 g/cm$^3$ at a temperature near 100° C. Accordingly, it enables for the wax to achieve a proper viscosity and difference in specific gravity from the liquid sample. Further, Paraffin Wax 115 is miscible with silicon oil, and it is thus also possible to mix silicon oil therewith to adjust viscosity. A liquid sample is an aqueous solution and thus is immiscible with wax. When the wax is melted, such a liquid sample is present in the form of droplets in the wax.

Thus, in the biochip 1 according to the first embodiment, the second chamber 20 is filled with the wax that is solid at room temperature (25° C.) or less. Therefore, liquid leakage or evaporation is suppressed, and this facilitates the handling and storage of the biochip. Further, the wax is liquid (oil) at a temperature range where PCR is performed. Therefore, the reaction can be performed easily without the need for a special treatment.

The second chamber 20 is formed as follows, for example. After a recess is formed in the substrate 50, a spacer is inserted into a space to be used as the sub-chamber 24, and the recess is filled with the wax 22. The spacer is then removed, and the top of the recess is closed with a cover 52. In this manner, a sub-chamber 24 having a desired volume can be formed easily.

The sub-chamber 24 may have disposed therein a primer for amplifying a target nucleic acid and/or a fluorescent probe for detecting a PCR product. As a result, when a liquid sample is dispensed, the liquid sample can be mixed with the primer and/or the fluorescent probe. Therefore, in the preparation of a liquid sample, the preparation of a primer and/or a fluorescent probe can be eliminated, and this further facilitates the dispensing operation.

The primer and/or the fluorescent probe may be disposed in a position in the second chamber 20 farthest from the injection path 30. As a result, after the wax 22 is melted, by applying thereto an inertial force from the first chamber 10 to the second chamber 20, such as centrifugal force, the dispensed liquid sample can be brought, with higher force, into contact with the primer and/or the fluorescent probe disposed in the second chamber 20. Therefore, the liquid sample can be mixed more easily with the primer and/or the fluorescent probe. Further, because of the presence of the wax 22 between the primer/fluorescent probe and the first chamber 10, the primer and the fluorescent probe are less likely to flow out into the first chamber 10.

The injection path 30 is formed between the first chamber 10 and the second chamber 20. The injection path 30 has such an inner diameter that a liquid sample or the melted wax 22 does not pass therethrough under gravity. For example, the inner diameter is about 0.1 mm or more and about 0.9 mm or less.

The injection path 30 limits the movement of a liquid sample or the melted wax 22 between the first chamber 10 and the second chamber 20. By applying an inertial force such as centrifugal force to a liquid sample placed in the first chamber 10, the liquid sample can be moved from the first chamber 10 to the sub-chamber 24 in the second chamber 20.

The inner walls of the first chamber 10, the second chamber 20, and the injection path 30 may be treated to be lipophilic and water repellent. A lipophilic, water-repellent material, such as polypropylene, may be used as a material for the substrate 50. As a result, after centrifugal force is applied to the biochip by rotation to dispense a liquid sample into the sub-chamber 24, when the rotation is stopped, the liquid sample is interrupted at the injection path 30 due to surface tension. The surplus of the liquid sample is separated from the liquid sample dispensed in the sub-chamber 24 and left in the first chamber 10. Accordingly, it is more likely that a precise amount of liquid sample is dispensed in the sub-chamber 24.

The first chamber 10 may be hydrophilic. As a result, it is more likely that the surplus of the liquid sample returns to the first chamber, and thus the liquid sample can be more reliably separated at the injection path 30.

Therefore, the biochip 1 according to the first embodiment allows a liquid sample to be accurately dispensed without using large-scale facilities, such as an automatic dispenser, in a simpler manner than pipetting and with greater precision than by pipetting.

Further, when the sub-chamber of the biochip 1 according to the first embodiment is filled with a liquid sample and mounted on a sample reaction apparatus, and a reaction is initiated, by the heating for the reaction, the wax is melted into a liquid state. No special treatment is required to initiate a reaction, so the reaction can be performed easily and efficiently.

2. Biochip of Second Embodiment

Figure 2A:
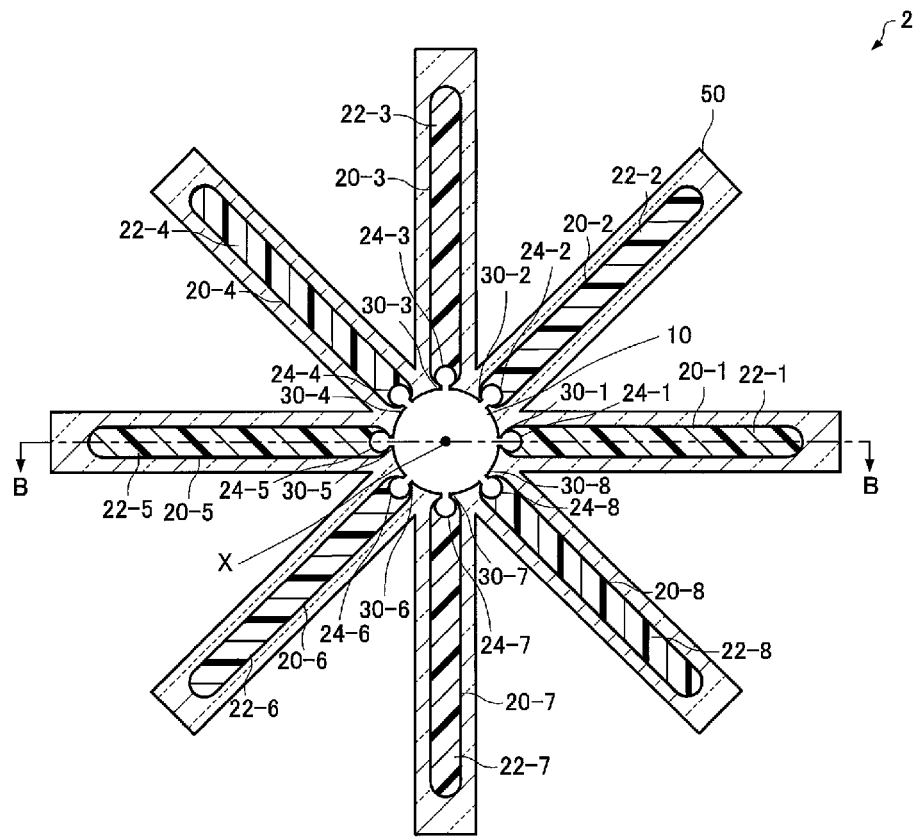
FIG. 2A is a plan view of a biochip according to a second embodiment.
Figure 2B:
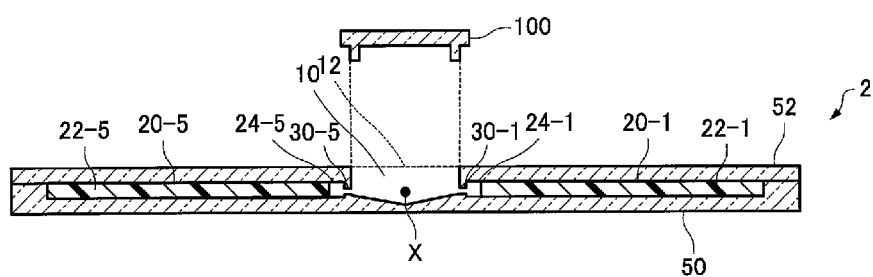
FIG. 2B is a cross-sectional view along line B-B of FIG. 2A.

FIG. 2A is a plan view of a biochip according to the second embodiment, and FIG. 2B is a cross-sectional view along line B-B of FIG. 2A. Hereinafter, the biochip 2 according to the second embodiment will be described, focusing on differences from the biochip 1 according to the first embodiment.

The biochip 2 according to the second embodiment includes a plurality of sets of second chambers 20-1 to 20-8 and injection paths 30-1 to 30-8. In the example shown in FIG. 2A and FIG. 2B, the second chamber 20-1 is paired with the injection path 30-1, the second chamber 20-2 with the injection path 30-2, the second chamber 20-3 with the injection path 30-3, the second chamber 20-4 with the injection path 30-4, the second chamber 20-5 with the injection path 30-5, the second chamber 20-6 with the injection path 30-6, the second chamber 20-7 with the injection path 30-7, and the second chamber 20-8 with the injection path 30-8. The biochip 2 includes eight such sets.

The biochip 2 includes a first chamber 10. The first chamber 10 communicates with the second chambers 20-1 to 20-8 via the injection paths 30-1 to 30-8, respectively.

Each of the second chambers 20-1 to 20-8 has the same configuration as the second chamber 20 of the biochip 1 according to the first embodiment. That is, the second chambers 20-1 to 20-8 are filled with waxes 22-1 to 22-8, respectively, and have formed therein sub-chambers 24-1 to 24-8, respectively. The walls of the sub-chambers 24-1 to 24-8 are at least partially made of the waxes 22-1 to 22-8, respectively.

In the example shown in FIG. 2A and FIG. 2B, the second chambers 20-1 to 20-8 are in the form of tubes whose longitudinal directions extend in the directions from the first chamber 10 to the injection paths 30-1 to 30-8, respectively. The shape of the second chambers 20-1 to 20-8 is not limited thereto. The second chambers 20-1 to 20-8 may be each in the form of a tube including a bent portion where the tube is bent at a certain angle. The second chambers 20-1 to 20-8 each may also have a partition portion that partitions a part of the inner region thereof, forming a channel that goes around the partition portion.

Each of the injection paths 30-1 to 30-8 has the same configuration as the injection path 30 of the biochip 1 according to the first embodiment. The injection paths 30-1 to 30-8 are in one imaginary plane and are disposed radially from a point X in the imaginary plane (hereinafter, the imaginary plane including the point X is simply referred to as "imaginary plane").

The first chamber 10 of the biochip 2 is closer to the point X than the injection paths 30-1 to 30-8. As a result, the first chamber 10 having placed therein a liquid sample can be rotated about a straight line perpendicular to the imaginary plane and passing through the point X to generate centrifugal force from the point X to the injection paths 30-1 to 30-8, thereby moving the liquid sample to the sub-chambers 24-1 to 24-8 of the second chambers 20-1 to 20-8 via the injection paths 30-1 to 30-8, respectively.

Therefore, the biochip 2 according to the second embodiment allows a liquid sample to be accurately dispensed from one first chamber to a plurality of sub-chambers without using large-scale facilities, such as an automatic dispenser, in a simpler manner than pipetting and with greater precision than by pipetting.

As in the case of the biochip 1 according to the first embodiment, the second chambers 20-1 to 20-8 are filled with the waxes that are solid at room temperature (25° C.) or less. Therefore, liquid leakage or evaporation is suppressed, and this facilitates the handling and storage of the biochip. The waxes are liquid (oil) at a temperature range where PCR is performed. Therefore, the reaction can be performed easily without the need for a special treatment.

The sub-chambers 24-1 to 24-8 each may have disposed therein a primer for amplifying a target nucleic acid and/or a fluorescent probe for detecting a PCR product. As a result, if a liquid sample is dispensed into the second chamber, the liquid sample can be mixed with the primer and/or the fluorescent probe. Therefore, in the preparation of a liquid sample, the preparation of a primer and/or a fluorescent probe can be eliminated, and this further facilitates the dispensing operation.

In each of the second chambers 20-1 to 20-8, the primer and/or the fluorescent probe may be disposed in a position farthest from the respective injection paths 30-1 to 30-8 that directly communicate with the second chambers 20-1 to 20-8. In the example shown in FIG. 2A and FIG. 2B, in each of the second chambers 20-1 to 20-8, a primer for amplifying a target nucleic acid and/or a fluorescent probe for determining the amount of PCR product is placed in a such position that the maximum centrifugal force is generated by rotation about a straight line perpendicular to the imaginary plane and passing through the point X. As a result, the dispensed liquid sample can be brought, with high force, into contact with the primer and/or the fluorescent probe disposed in each of the second chambers 20-1 to 20-8. Therefore, the liquid sample can be mixed more easily with the primer and/or the fluorescent probe. Further, the primer and the fluorescent probe are less likely to flow out into the first chamber 10.

3. Sample Reaction Apparatus

Figure 3A:
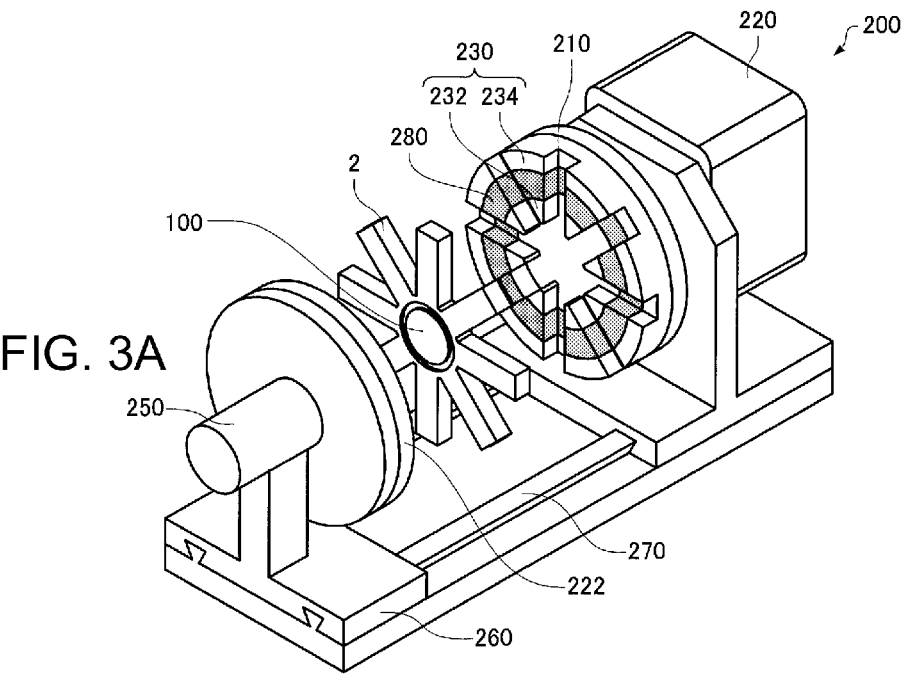
FIG. 3A is a perspective view of a sample reaction apparatus according to a third embodiment.
Figure 3B:
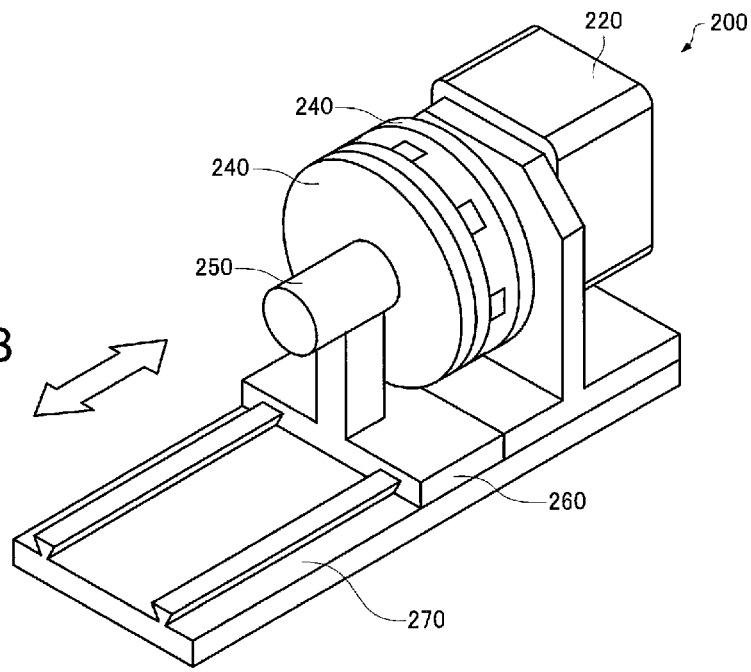
FIG. 3B is another perspective view of the sample reaction apparatus.

FIG. 3A is a perspective view of a sample reaction apparatus according to a third embodiment, and FIG. 3B is another perspective view of the sample reaction apparatus.

A sample reaction apparatus 200 according to this embodiment is a sample reaction apparatus that performs a sample reaction using a biochip. In the case where the biochip 1 is used, the sample reaction apparatus 200 includes a holder 210 that holds the biochip 1; a rotor 220 that rotates the biochip 1 in a case that the holder 210 holds the biochip 1 to vary the distance between a gravitationally lowest point in the second chamber 20 and the axis of rotation; and a heating unit 230 for heating at least a part of the second chamber 20 in a case that the holder 210 holds the biochip 1 to a temperature not less than the melting point of the wax 22 so that the biochip 1 has a symmetrical temperature distribution about the axis of rotation.

In the case where the biochip 2 is used, the sample reaction apparatus 200 includes a holder 210 that holds the biochip 2; a rotor 220 that rotates the biochip 2 in a case that the holder 210 holds the biochip 1 to vary the distances between gravitationally lowest points in the second chambers 20-1 to 20-8 and the axis of rotation; and a heating unit 230 heating at least a part of the second chambers 20-1 to 20-8 in a case that the holder 210 holds the biochip 1 to a temperature not less than the melting point of the waxes 22-1 to 22-8 so that the biochip 2 has a symmetrical temperature distribution about the axis of rotation.

Hereinafter, the sample reaction apparatus 200 that uses the biochip 2 will be taken as an example and described with reference to FIG. 3A and FIG. 3B.

The holder 210 is configured to be capable of receiving the biochip 2 mounted thereon. In the example shown in FIG. 3A, a groove that mates with the biochip 2 serves as the holder 210. As shown in FIG. 3B, it is possible to form a slide 260 movable along a slide guide 270 in the direction indicated by a white arrow, and press the biochip 2 against the holder 210 to hold the biochip 2 on the holder 210.

With the biochip 2 being holded on the holder 210, the rotor 220 rotates the biochip 2 to vary the distances between gravitationally lowest points in the second chambers 20-1 to 20-8 and the axis of rotation. In the example shown in FIG. 3A, with the biochip 2 being mounted on the holder 210, the rotor 220 rotates the biochip 2 about a straight line perpendicular to the imaginary plane and passing through the point X, thereby varying the distances between gravitationally lowest points in the second chambers 20-1 to 20-8 and the axis of rotation.

With the biochip 2 being mounted on the holder 210, the heating unit 230 heats at least a part of the second chambers 20-1 to 20-8 to a temperature not less than the melting point of the waxes 22-1 to 22-8 so that the biochip 2 has a symmetrical temperature distribution about the axis of rotation. In the example shown in FIG. 3A, the heating unit 230 includes a high-temperature heater 232 on the side relatively close to the axis of rotation, which performs heating at relatively high temperatures, and a low-temperature heater 234 on the side relatively far from the axis of rotation, which performs heating at relatively low temperatures. This forms a temperature gradient where the temperature decreases outward from the vicinity of the axis of rotation. That is, in the example shown in FIG. 3A, the heating unit 230 is configured to heat the biochip 2 so that the biochip 2 has an axisymmetrical temperature distribution.

The heating unit 230 may be configured to be controlled by a controller 250. When the sample reaction apparatus 200 is used for real-time PCR, the heating unit 230 may be controlled so that the temperature of the high-temperature heater 232 is 95° C. and the temperature of the low-temperature heater 234 is 60° C. In addition, as shown in FIG. 3A, the heating unit 230 may include a heat insulating material 280 between the high-temperature heater 232 and the low-temperature heater 234. Further, as shown in FIG. 3B, heat insulating materials 240 may be disposed to sandwich the heating unit 230.

The waxes 22-1 to 22-8 heated by the heating unit 230 are melted into a liquid state. If a liquid sample is supplied to the second chambers 20-1 to 20-8, because of the difference in specific gravity between the melted waxes and the liquid sample, the liquid sample heavier than the waxes moves to the vicinity of a gravitationally lowest point in each of second chambers 20-1 to 20-8. The biochip 2 is heated by the heating unit 230 to have an axisymmetrical temperature distribution, and, therefore, as the distances between gravitationally lowest points in the second chambers 20-1 to 20-8 and the axis of rotation vary, regions of different temperatures serve as gravitationally lowest points. Accordingly, by suitably controlling the rotor 220 and the heating unit 230, a liquid sample can be moved among regions of different temperatures in the second chambers 20-1 to 20-8, and thus the liquid sample can be subjected to a desired thermal cycle.

As a result, a sample reaction apparatus for performing a sample reaction using a biochip that allows a liquid sample to be accurately dispensed in a simple manner is achieved.

4. Sample Reaction Method

Figure 4:
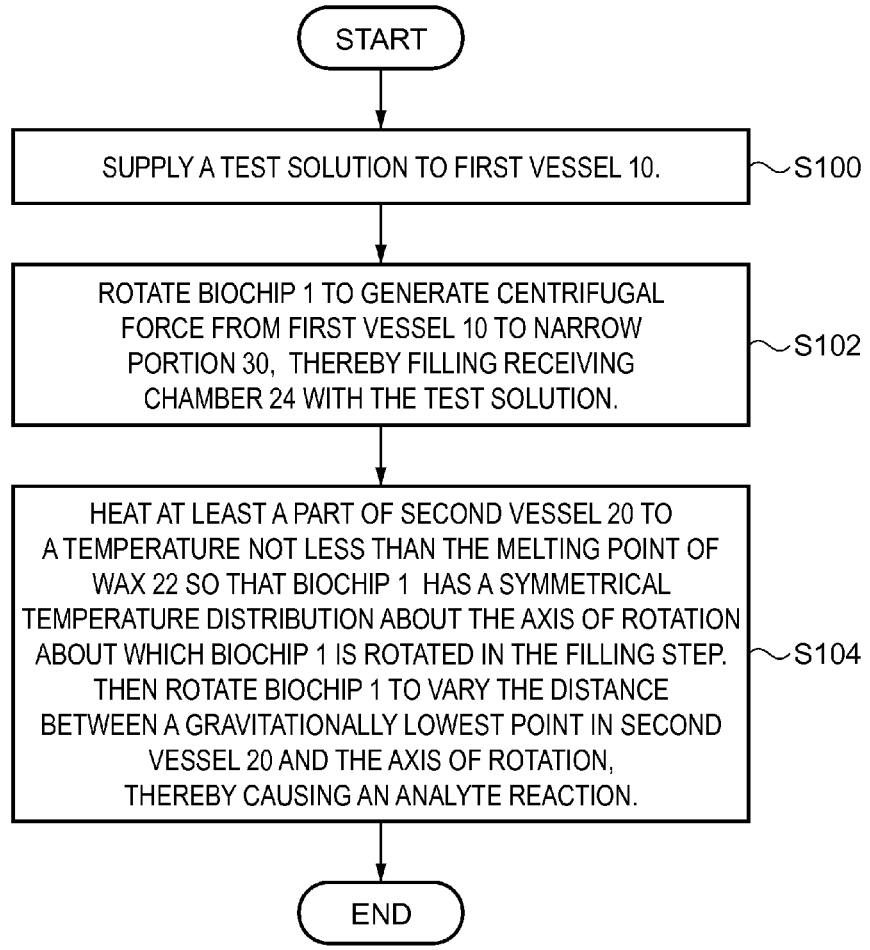
FIG. 4 shows an example of a flow chart of a sample reaction method according to a fourth embodiment.

FIG. 4 shows an example of a flow chart of a sample reaction method according to a fourth embodiment. Although the biochip 1 according to the first embodiment is used as a biochip in the example shown in FIG. 4, the biochip 2 according to the second embodiment may also be used.

The sample reaction method shown in FIG. 4 is a sample reaction method using the biochip 1. The sample reaction method includes supplying a liquid sample (test solution) to the first chamber 10; filling the sub-chamber 24 with the liquid sample by rotating the biochip 1 about the axis of rotation to generate centrifugal force from the first chamber 10 to the injection path 30; and performing a sample reaction by heating at least a part of the second chamber 20 to a temperature not less than the melting point of the wax 22 so that the biochip 1 has a symmetrical temperature distribution about the axis of rotation, and then rotating the biochip 1 to vary the distance between a gravitationally lowest point in the second chamber 20 and the axis of rotation.

First, the supplying step is performed, in which a liquid sample is supplied to the first chamber 10 (step S100). For example, a liquid sample is placed into the first chamber 10 through the inlet 12 of the biochip 1, thereby supplying the liquid sample to the first chamber 10.

After the step S100, the filling step is performed, in which the biochip 1 is rotated to generate centrifugal force from the first chamber 10 to the injection path 30, thereby filling the sub-chamber 24 with the liquid sample (step S102). The biochip 1 is rotated to generate centrifugal force from the first chamber 10 to the injection path 30 using a centrifuge or the like, thereby filling the sub-chamber 24 with the liquid sample. This filling step allows the liquid sample to be accurately dispensed in a simple manner.

After the step S102, the sample reaction step is performed, in which at least a part of the second chamber 20 is heated to a temperature not less than the melting point of the wax 22 so that the biochip 1 has a symmetrical temperature distribution about the axis of rotation, and then the biochip 1 is rotated to vary the distance between a gravitationally lowest point in the second chamber 20 and the axis of rotation, thereby performing a sample reaction (step S104). It is preferable that the apparatus for applying centrifugal force in the dispensing step is different from the reaction apparatus used in the reaction step.

The wax 22 is heated to a temperature not less than the melting point thereof, and thus melted into a liquid state. Because of the difference in specific gravity between the melted wax and the liquid sample, the liquid sample heavier than the wax moves to the vicinity of a gravitationally lowest point in the second chamber 20. The biochip 1 is heated to have an axisymmetrical temperature distribution, and, therefore, the temperature varies with changes in the distance between the gravitationally lowest point in the second chamber 20 and the axis of rotation. Accordingly, by suitably controlling the rotation and the heating temperature, a liquid sample can be moved among regions of different temperatures in the second chamber 20, and thus the sample can be subjected to a desired thermal cycle. As a result, a sample reaction can be performed using the biochip 1.

The sub-chamber 24 may have disposed therein a primer for amplifying a target nucleic acid and/or a fluorescent probe for detecting a PCR product. As a result, when a liquid sample is dispensed, the liquid sample can be mixed with the primer and/or the fluorescent probe. Therefore, in the preparation of a liquid sample, the preparation of a primer and/or a fluorescent probe can be eliminated, and this further facilitates the dispensing operation.

The primer and/or the fluorescent probe may be disposed in a position in the second chamber 20 farthest from the injection path 30. As a result, the dispensed liquid sample can be brought, with higher force, into contact with the primer and/or the fluorescent probe disposed in the second chamber 20. Therefore, the liquid sample can be mixed more easily with the primer and/or the fluorescent probe. Further, the primer and the fluorescent probe are less likely to flow out into the first chamber 10.

Figure 5:
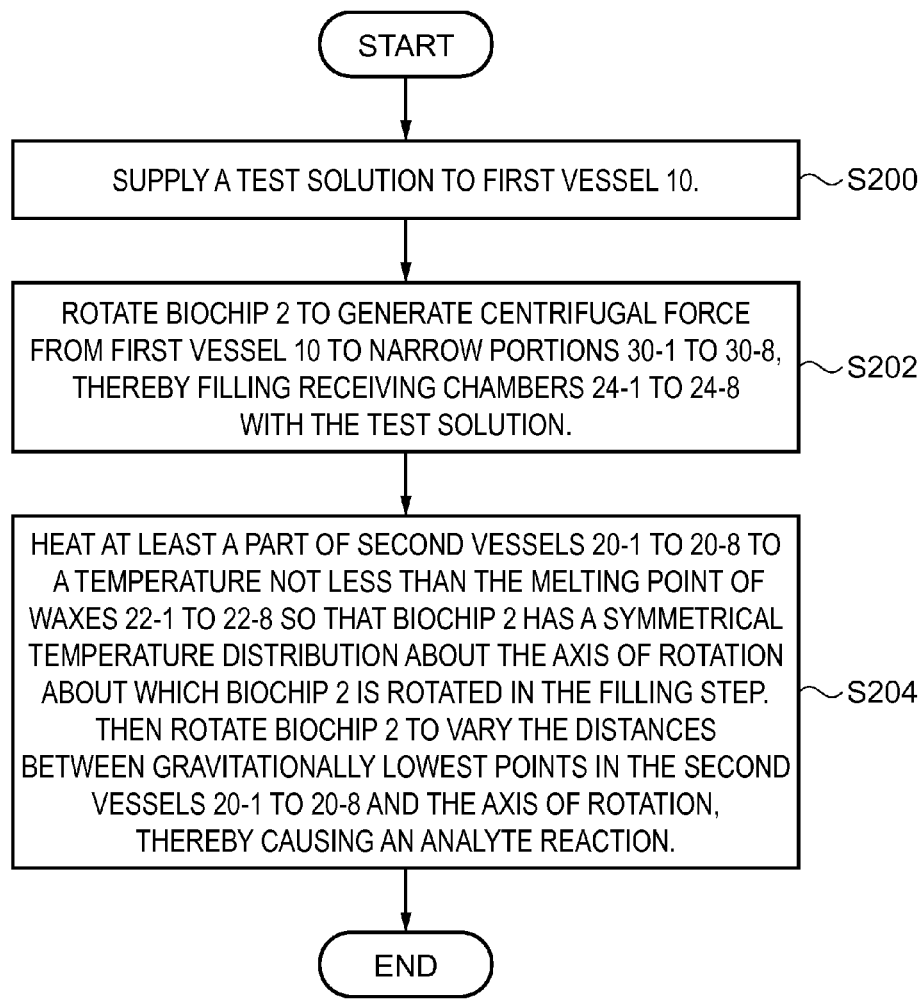
FIG. 5 shows another example of a flow chart of a sample reaction method according to the fourth embodiment.

FIG. 5 shows another example of a flow chart of a sample reaction method according to the fourth embodiment. In the example shown in FIG. 5, the biochip 2 according to the second embodiment is used as a biochip.

The sample reaction method shown in FIG. 5 is a sample reaction method using the biochip 2. The sample reaction method includes supplying a liquid sample to the first chamber 10; filling the sub-chambers 24-1 to 24-8 with the liquid sample by rotating the biochip 2 about the axis of rotation to generate centrifugal force from the first chamber 10 to the injection paths 30-1 to 30-8; and performing a sample reaction by heating at least a part of the second chambers 20-1 to 20-8 to a temperature not less than the melting point of the waxes 22-1 to 22-8 so that the biochip 2 has a symmetrical temperature distribution about the axis of rotation, and then rotating the biochip 2 to vary the distances between gravitationally lowest points in the second chambers 20-1 to 20-8 and the axis of rotation.

First, the supplying step is performed, in which a liquid sample is supplied to the first chamber 10 (step S200). A liquid sample is placed into the first chamber 10 through the inlet 12 of the biochip 2, thereby supplying the liquid sample to the first chamber 10.

After the step S200, the filling step is performed, in which the biochip 2 is rotated to generate centrifugal force from the first chamber 10 to the injection paths 30-1 to 30-8, thereby filling the sub-chambers 24-1 to 24-8 with the liquid sample (step S202). It is also possible to rotate the biochip 2 about a straight line perpendicular to the imaginary plane and passing through the point X using a centrifuge or the like, thereby filling the sub-chambers 24-1 to 24-8 with the liquid sample. The filling step allows the liquid sample to be accurately dispensed in a simple manner.

After the step S202, the sample reaction step is performed, in which at least apart of the second chambers 20-1 to 20-8 is heated to a temperature not less than the melting point of the waxes 22-1 to 22-8 so that the biochip 2 has a symmetrical temperature distribution about the axis of rotation about which the biochip 2 is rotated in the filling step, and then the biochip 2 is rotated to vary the distances between gravitationally lowest points in the second chambers 20-1 to 20-8 and the axis of rotation, thereby causing a sample reaction (step S204).

The waxes 22-1 to 22-8 are heated to a temperature not less than the melting point thereof, and thus melted into a liquid state. Because of the difference in specific gravity between the melted waxes and the liquid sample, the liquid sample heavier than the waxes moves to the vicinity of a gravitationally lowest point in each of second chambers 20-1 to 20-8. The biochip 2 is heated to have an axisymmetrical temperature distribution, and, therefore, the temperature varies with changes in the distance between the gravitationally lowest point in each of the second chambers 20-1 to 20-8 and the axis of rotation. Accordingly, by suitably controlling the rotation and the heating temperature, a liquid sample can be moved among regions of different temperatures in the second chambers 20-1 to 20-8, and thus the sample can be subjected to a desired thermal cycle. As a result, a sample reaction can be performed using the biochip 2.

The sub-chambers 24-1 to 24-8 each may have disposed therein a primer for amplifying a target nucleic acid and/or a fluorescent probe for detecting a PCR product. As a result, when a liquid sample is dispensed, the liquid sample can be mixed with the primer and/or the fluorescent probe. Therefore, in the preparation of a liquid sample, the preparation of a primer and/or a fluorescent probe can be eliminated, and this further facilitates the dispensing operation.

In each of the second chambers 20-1 to 20-8, the primer and/or the fluorescent probe may be disposed in a position farthest from the respective injection paths 30-1 to 30-8 that directly communicate with the second chambers 20-1 to 20-8. As a result, the dispensed liquid sample can be brought, with higher force, into contact with the primer and/or the fluorescent probe disposed in the second chambers 20-1 to 20-8. Therefore, the liquid sample can be mixed more easily with the primer and/or the fluorescent probe. Further, the primer and the fluorescent probe are less likely to flow out into the first chamber 10.

The above embodiments and variations are mere examples, and the invention is not limited thereto. For example, it is also possible to suitably combine some of the embodiments and variations.

The invention is not limited to the above embodiments, and further variations are possible. The invention encompasses configurations that are essentially the same as the configurations described in the embodiments (e.g., configurations with the same functions, methods, and results, or configurations with the same objects and advantages). The invention encompasses configurations obtained by changing non-essential parts of the configurations described in the embodiments. The invention encompasses configurations that have the same functions and advantages or achieve the same objects as the configurations described in the embodiments. The invention encompasses configurations obtained by adding related art to the configurations described in the embodiments.

What is claimed is:

1. A biochip comprising:
   a first chamber;
   a second chamber that is filled with a wax, a melting point of the wax being from 25° C. to 63° C.;
   an injection path between the first chamber and the second chamber, wherein the injection path has an inner diameter of from about 0.1 mm to about 0.9 mm such that a liquid sample does not pass therethrough under gravity; and
   a sub-chamber that includes a wall at least partially made of the wax, the sub-chamber is formed inside the second chamber and communicates with the first chamber via the injection path.

2. A biochip according to claim 1, wherein
   the biochip includes a plurality of sets, each one of the set includes the second chamber and the injection path,
   the injection paths are in one plane and disposed radially from a point in the plane, and
   the first chamber is closer to the point than the injection paths.

3. A biochip according to claim 1, wherein a primer and/or a fluorescent probe is disposed in the sub-chamber.

4. A biochip according to claim 1, wherein a primer and/or a fluorescent probe is disposed in the second chamber farthest from the injection path.

5. A sample reaction apparatus comprising:
   a holder that holds a biochip, the biochip including:
   a first chamber;
   a second chamber filled with a wax, a melting point of the wax being from 25° C. to 63° C.;
   an injection path between the first chamber and the second chamber, wherein the injection path has an inner diameter of from about 0.1 mm to about 0.9 mm such that a liquid sample does not pass therethrough under gravity; and
   a sub-chamber that includes a wall at least partially made of the wax, the sub-chamber is formed inside the second chamber and communicates with the first chamber via the injection path;
   a rotor that rotates the biochip in a case that the holder holds the biochip to vary the distance between a gravitationally lowest point in the second chamber and an axis of rotation; and
   a heating unit that heats at least a part of the second chamber in a case the holder holds the biochip to a temperature not less than the melting point of the wax so that the biochip has a symmetrical temperature distribution about the axis of rotation.

6. A sample reaction method comprising:
   supplying a liquid sample to the first chamber of a biochip, the biochip comprising:
   the first chamber;
   a second chamber filled with a wax, a melting point of the wax being 25° C. or more and 63° C. or less;
   an injection path between the first chamber and the second chamber; and
   a sub-chamber that includes a wall at least partially made of the wax, the sub-chamber is formed inside the second chamber and communicates with the first chamber via the injection path;
   filling the sub-chamber with the liquid sample by rotating the biochip about an axis of rotation to generate centrifugal force from the first chamber to the injection path; and
   performing a sample reaction by heating at least a part of the second chamber to a temperature not less than the melting point of the wax so that the biochip has a symmetrical temperature distribution about the axis of rotation, and then rotating the biochip to vary the distance between a gravitationally lowest point in the second chamber and the axis of rotation.

* * * * *